United States Patent [19]

Lucido

[11] 4,314,158
[45] Feb. 2, 1982

[54] ELECTRON APPLICATOR FOR A LINEAR ACCELERATOR

[75] Inventor: Donald R. Lucido, Martinez, Calif.

[73] Assignee: Siemens Medical Laboratories, Inc., Walnut Creek, Calif.

[21] Appl. No.: 136,359

[22] Filed: Apr. 1, 1980

[51] Int. Cl.³ .......................... G02B 5/00; H01J 29/46
[52] U.S. Cl. ................................. 250/505; 250/310; 285/DIG. 22; 313/458
[58] Field of Search ........................ 250/505, 310, 311; 222/567; 285/DIG. 22, 319; 403/109; 313/458; 128/404

[56] References Cited

U.S. PATENT DOCUMENTS

| | | | |
|---|---|---|---|
| 1,600,867 | 9/1926 | Coolidge | 250/505 |
| 2,452,219 | 10/1948 | Bergvall et al. | 285/DIG. 22 |
| 2,846,587 | 8/1958 | Thurow | 250/505 |
| 2,991,362 | 7/1961 | Schumacher | 250/310 |
| 3,245,703 | 4/1966 | Manly | 285/DIG. 22 |
| 3,720,828 | 3/1973 | Nablo | 250/311 |
| 3,936,646 | 2/1976 | Jonker | 250/505 |
| 4,053,808 | 10/1977 | Peacock | 313/458 |

OTHER PUBLICATIONS

"Mevatron 12 Data", Siemens Aktiengesellschaft, Erlangen, Germany, Order No. MT 3/7137.

*Primary Examiner*—Harold A. Dixon
*Attorney, Agent, or Firm*—Spellman, Joel and Pelton

[57] ABSTRACT

The electron applicator incorporates a stationary support tube and an insert tube. The support tube and the insert tube each have a first end portion and a second end portion. The first end portion of the insert tube slideably extends into the second end portion of the support tube. Electrons of high energy are transmitted through the assembly of both tubes. The surface of the insert tube is tapered inwardly toward the end thereof in the travelling direction of the high energy electrons. A device is provided for preventing the insert tube from sliding out of the support tube. A first engaging device engages the insert tube in a first working position. This device is such that upon a predetermined axial force which may inadvertently be exercised by a patient under treatment, the insert tube will slide into the support tube.

An adapter for small field or cavetory treatment may be connected to the output end of the insert tube. To compensate for the additional length of the tube assembly associated with such an adapter, the insert tube is moved into the support tube by a distance equal to the effective length increase and held in this second position by a second engaging device which can be similar to the first engaging device.

9 Claims, 2 Drawing Figures

ELECTRON APPLICATOR FOR A LINEAR ACCELERATOR

FIELD OF THE INVENTION

This invention relates to a linear accelerator useful for radiotherapy of patients. In particular, this invention relates to the collimator assembly of a linear accelerator. Still more particularly, this invention relates to an electron applicator for a linear accelerator.

BACKGROUND OF THE INVENTION

In the wave guide of a linear accelerator, electrons are accelerated at high energy. The electrons leave the wave guide through an exit window and enter a collimator assembly. The collimator assembly forms an electron field of a given size at a predetermined distance from the exit window. This electron field is applied to the patient under treatment. The end part of the collimator assembly which is next to the patient will be called herein the "electron applicator". In some linear accelerators, (see, for instance, brochure "Mevatron 12", Siemens AG Erlangen, West Germany, No. MT 3/7137), the total length from the exit window to the end of the applicator is chosen to have a definite value, for instance, 1 meter, to define the dose rate (for example, 300 R/min) of electron radiation.

It is desirable to have applicators with different end openings and therefore different electron field sizes for the treatment of malicious tissues of different sizes. It is also desirable to have applicators which do not hurt the patient in case the patient should inadvertently touch the end of the applicator.

In the field of linear accelerators, the so-called Henschke electron applicator is known. This applicator is essentially an assembly of an outer or support tube and an inner or insert tube. The support tube is stationary and connected to the collimator. An upper portion of the insert tube is slideably mounted inside the support tube. Both tubes are of cylindrical shape.

Electron collimators and electron applicators are known in the field of accelerators. An electron beam collimator is described in U.S. Pat. No. 4,053,808, and an electron applicator is disclosed in U.S. patent application Ser. No. 871,200 now U.S. Pat. No. 4,220,866.

OBJECTS OF THE INVENTION

An object of this invention is to provide an improved electron applicator for a linear accelerator.

Another object of this invention is to provide a Henschke electron applicator with additional safety features for the patient under treatment.

Another object of this invention is to provide an electron applicator having a uniform electron distribution across its output end.

Still another object of this invention is to provide an electron applicator having means to retain the insert tube safely within the support tube.

Still another object of the invention is to provide an electron applicator the insert tube of which is easily interchangeable.

Still another object of this invention is to provide an electron applicator having an electron field size freely selectable independently of the connection of the support tube to a collimator plate.

Still another object of this invention is to provide an electron applicator with an adaptor for intercavity applications, wherein the total length from the exit window of the electron accelerator to the end of the adapter equals the predetermined total length between the exit window and the output of the insert tube when the adapter is not present.

SUMMARY OF THE INVENTION

According to this invention, an electron applicator for a linear accelerator incorporates a stationary support tube and an insert tube. The support tube and the insert tube each have a first end portion and a second end portion. The first end portion of the insert tube slideably extends into the second end portion of the support tube. Electrons of high-energy are transmitted through the assembly of both tubes. The surface of the insert tube is tapered inwardly longitudinally toward the end thereof in the travelling direction of the high-energy electrons. A device is provided for preventing the insert tube from sliding out of the support tube. A first engaging device engages the insert tube in a first working position. This device is such that upon a predetermined axial force which may inadvertently be exercised by a patient under treatment, the insert tube will slide into the support tube.

An adapter for small field or cavetory treatment may be connected to the output end of the insert tube. To compensate for the additional length of the tube assembly associated with such an adapter, the insert tube is moved into the support tube by a distance equal to the effective length increase and held in this second position by a second engaging device which can be similar to the first engaging device.

The foregoing and other objects, features and advantages of the invention will be apparent from the following more particular description of the preferred embodiment of the invention, as illustrated in the accompanying drawings.

DESCRIPTION OF THE PREFERRED EMBODIMENT

Figure 1:
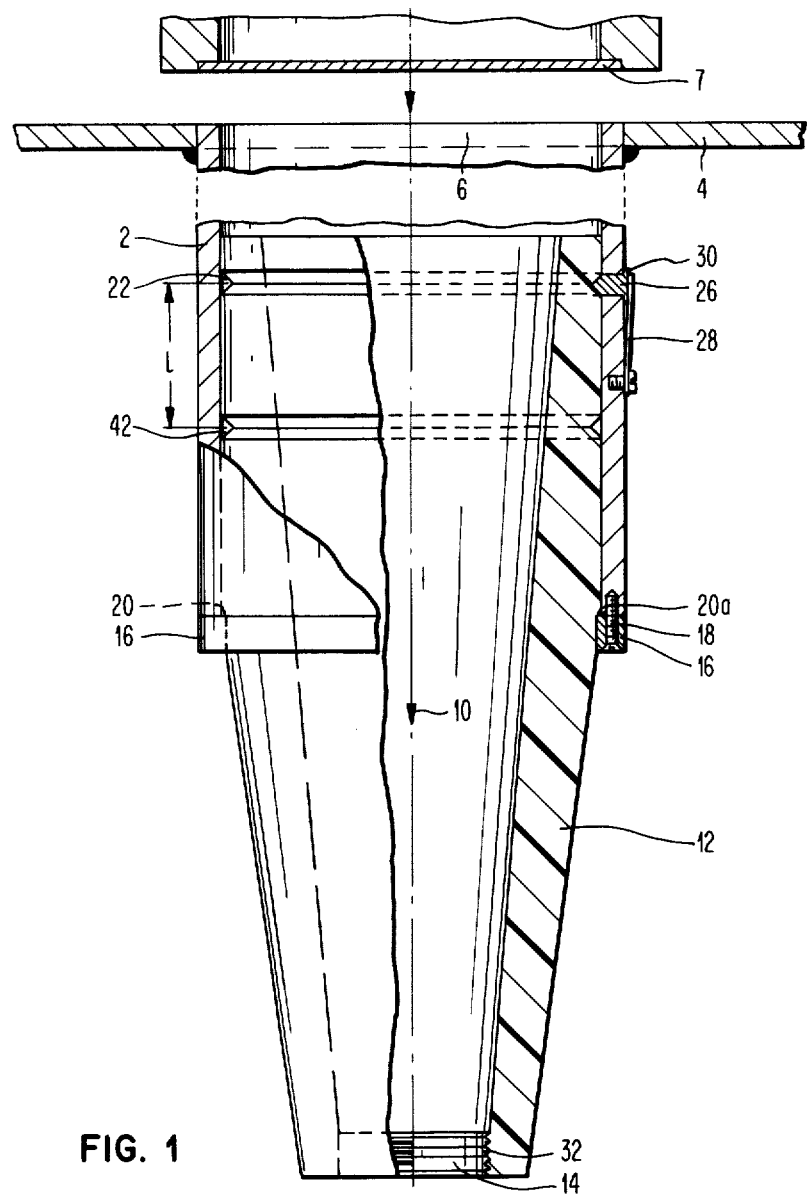
FIG. 1 is a cross-sectional view of an electron applicator for a linear accelerator according to the invention.

In FIG. 1 is illustrated an electron applicator for a linear accelerator. A cylindrical support tube 2 is positioned with its tube axis vertically. The upper end of the support tube 2 is connected to a stationary plate 4 having a circular opening 6. The plate 4 is part of the collimator assembly (not shown) of the accelerator and therefore may be termed collimator plate. The collimator assembly is of a well known commonly used type. High energy electrons which are emitted from the exit window 7 of the accelerator travel through the collimator assembly and the opening 6 into the upper end portion of the support tube 2. The main travelling direction which coincides with the tube axis is designated by an arrow 10.

The support tube 2 may consist of a metal such as aluminum. The connection to the rim of the opening 6 may be performed by welding.

In a first working position, which is shown in FIG. 1, an elongated insert tube 12 slideably extends to a certain length into the lower end of the stationary support tube 2. The upper portion of the insert tube 12 (which extends into the support tube 2) has a cylindrical outer surface, whereas the outer surface of the lower portion is tapered in the direction of the arrow 10. The inner diameter of the support tube 2 is slightly larger than the outer diameter of the upper portion of the insert tube 12. Thus, the insert tube 12 may slide in the support tube 2 along the tube axis.

The high energy electrons received from the upper portion of the support tube 2 are transmitted through the insert tube 12 and discharged at the lower portion of the insert tube 12 through an opening 14 of preferably circular cross-section. In treatment of a patient, the opening 14 serves as an electron orifice.

The inner surface of the insert tube 12 is tapered along the tube axis (=arrow 10) throughout its entire length. This is of particular importance since an undesirable build-up of electrons close to the edges of the orifice 14 can thus be avoided. In contrast to such a build-up, the electron distribution measured across the orifice 14 of the insert tube 12 is uniform or of a slight U-shape. In treatment of a patient, inflammatory rings on the skin of the patient exposed to the electrons thus can be avoided. This is an important safety measure.

The insert tube 12 preferably may be made of a plastic such as Lucite. As will be apparent later, the insert tube 12 is easily interchangeable with other insert tubes having openings 14 of different sizes in order to obtain various electron field sizes. The opening 14 of an insert tube 12 may be, for instance, 2, 4, 6 or 8 cm in diameter, depending on the size of the patient's skin to be irradiated. The thickness of the wall at the opening 14 may be, for instance, 1 cm, depending on the material used.

An annular retaining collar 16 is provided at the lower end of the support tube 2 attached by any suitable means such as screws 18 to permit the collar 16 to be easily disconnected and removed. The inner diameter of the collar 16 may be to a certain degree smaller than the inner diameter of the support tube 2 so as to form an annular supporting shoulder or rim 20. The outer surface of the inner or insert tube 12 has a complementary annular shoulder 20a to rest on the supporting shoulder 20 of the retaining collar 16. In the first operating position shown in FIG. 1, the shoulder 20a of the insert tube 12 may rest on the shoulder 20 of the collar 16.

The retaining collar 16 is part of a device which retains the insert tube 12 in the first working position shown in FIG 1. This is another important safety aspect of the illustrated applicator.

The location of the rim 20 and the lengths of the tubes 2 and 12 are chosen such that the total length from the exit window 7 to the lower end face of the insert tube 12 equals a predetermined value, for instance, 1 meter.

A positioning device resiliently engages the insert tube 12 in the first working position. This positioning device is formed by a first annular slot or groove 22 in the outer surface of the upper portion of the insert tube 12 and a retaining pin 26 which is spring-loaded by a leaf spring 28 mounted on the outer wall of the support tube 2. The spring 28 resiliently engages the cap 30 of the pin 26 which extends through the wall of the support tube 2. Alternatively the pin 26 may be attached to the end of the spring 28. In the first working position, the pin 26 extends through the hole 24 into the first groove 22. The first groove 22 and the tip of the pin 26 are preferably V-shaped. This positioning device ensures that the insert tube 12 will slide in the support tube 2 in an upward direction as soon as an axial force (which is predetermined by the spring 28) is exceeded, as for example, should a patient inadvertently strike the lower end of the insert tube 12. This is another important safety aspect of the illustrated electron applicator.

Due to the cone-shape of its lower part, the electron applicator may be applied to almost all skin portions of the human body. Even intercavitory applications are possible if the required field size is not too large.

Figure 2:
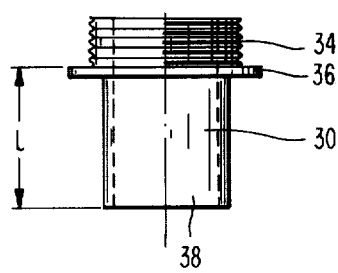
FIG. 2 shows a side elevational view of an adapter for intercavity application which can be attached to and used with the electron applicator of FIG. 1.

For treatment of small cavities, such as the mouth, or small desease fields a cylindrical adapter 30 (see FIG. 2) may be used. The adapter 30 has a smaller outer diameter than the insert tube 2 at its lower end. The adapter 30 is T-shaped. For the mentioned medical application, the adapter 30 will be connected to the lower end portion of the insert tube 12. The adapter 30 may preferably be made of plastic. However, it is also possible to make it of a metal like brass.

For receiving the adapter 30, an internal thread 32 (see FIG. 1) is formed at the lower end portion of the insert tube 12. The adapter 30 has a corresponding external thread 34 on its upper part. The diameter of the disc-shaped middle part 36 is equal to the outer diameter of insert tube 12 at the orifice 14.

When the adapter 30 is connected to the lower end of the insert tube 12, the mentioned total length from the exit window 7 to the electron orifice, which is now the lower opening 38 of the adapter 30, would be increased by the length l, which is equal to the distance from the upper side of the middle part 36 to the lower end of the adapter 30. In order to compensate for this length increase, the insert tube 12 is moved in an upward direction by the length l to arrive in a second working position.

There is provided a second positioning or retaining device for resiliently engaging the insert tube 12 in this second working position. The engagement is again such that upon a predetermined axial force, which might be inadvertently exerted by a patient, the insert tube 12 may farther slide into the support tube 2.

The second engaging device for engaging the insert tube 12 in the second working position comprises a second annular groove 42 which is located in the outer surface of the insert tube 12 lower than the first groove 22. The distance between the grooves 22 and 42 is equal to l. The second groove 42 may also be V-shaped. In the second working position the retaining pin 26 extends through the hole 24 into the second groove 42. Again, should a force strike or be exerted against the lower end, now at adapter 30, the insert tube 12 will slide upwardly.

In medical applications, the electron output of the adapter 30 may be made small enough to reach a part of the head, neck areas, or cavities like the mouth.

While the electron applicator described above constitutes a preferred embodiment, it is to be understood that a variety of changes may be made without affecting the range and scope of this invention.

What is claimed is:

1. An electron applicator for a linear accelerator, comprising in combination:
    (a) a stationary support tube for transmitting high-energy electrons therethrough, said support tube having a first end portion for receiving said electrons and a second end portion;
    (b) an insert tube for transmitting said high-energy electrons therethrough, said insert tube having a first end portion extending slideably into the second end portion of said support tube, and a second end portion for discharging said electrons, and an outer and an inner surface, said inner surface being tapered longitudinally along the path of said high-energy electrons;

(c) means for retaining said insert tube within said support tube;

(d) first means for resistibly engaging said insert tube in a selected first working position such that upon a predetermined axial force said insert tube slides farther into said support tube; and (e) second means for resistibly engaging said insert tube in a selected working position such that upon a predetermined axial force said insert tube slides farther into said support tube, said second working position being spaced from said first working position.

2. The electron applicator according to claim 1, wherein said retaining means comprise a rim in the outer surface of said insert tube and a retaining collar on the face of the second end portion of said support tube, said rim engaging said collar when said insert tube is in said first working position.

3. The electron applicator according to claim 2, wherein said retaining collar is a ring attached to the face of the second end portion of said support tube.

4. The electron applicator according to claim 1, wherein said first engaging means comprise a first annular groove in the outer surface of said first end portion of said insert tube, said support tube having a hole in the side thereof and a spring loaded pin, said pin extending through said hole into said first groove when said insert tube is in said first working position.

5. The electron applicator according to claim 4, wherein said first groove and the tip of said pin are V-shaped.

6. The electron applicator according to claim 1, wherein the outer surface of the second end portion of said insert tube is tapered in the travelling direction of said high energy electrons.

7. The electron applicator according to claim 1, having means in the second end portion of said insert tube for receiving an adapter.

8. The electron applicator according to claim 7, wherein a thread is formed in the inner surface of said insert tube and wherein said adapter is T-shaped.

9. The electron applicator according to claim 1, wherein said second engaging means for engaging said insert tube in said second working position comprise a second annular groove in the outer surface of said first end portion of said insert tube, said support tube having a hole in the side thereof and a spring loaded pin, said pin extending through said hole into said second groove when said insert tube is in said second working position.

* * * * *